US006605701B2

(12) United States Patent
Schnepf et al.

(10) Patent No.: US 6,605,701 B2
(45) Date of Patent: Aug. 12, 2003

(54) **PESTICIDAL TOXINS AND GENES FROM *BACILLUS LATEROSPORUS* STRAINS**

(75) Inventors: H. Ernest Schnepf, San Diego, CA (US); Kenneth E. Narva, San Diego, CA (US); Brian A. Stockhoff, San Diego, CA (US); Stacey Finstad Lee, San Diego, CA (US); Mikki Walz, Poway, CA (US); Blake Sturgis, Solana Beach, CA (US)

(73) Assignee: Mycogen Corporation, Indianapolis, IN (US)

( * ) Notice: Subject to any disclaimer, the term of this patent is extended or adjusted under 35 U.S.C. 154(b) by 0 days.

(21) Appl. No.: 09/967,805

(22) Filed: Sep. 28, 2001

(65) Prior Publication Data

US 2002/0120114 A1 Aug. 29, 2002

Related U.S. Application Data

(63) Continuation of application No. 09/371,913, filed on Aug. 10, 1999, now Pat. No. 6,297,369.

(60) Provisional application No. 60/095,955, filed on Aug. 10, 1998, and provisional application No. 60/138,251, filed on Jun. 8, 1999.

(51) Int. Cl.[7] ........................ C07H 21/02; C07K 14/00; C12N 5/04

(52) U.S. Cl. ........................... 530/350; 514/12; 514/44; 435/252.3; 435/252.5; 435/410; 435/440; 435/91.4; 435/468; 435/471; 435/476; 435/480; 536/23.1; 536/23.7; 536/23.71

(58) Field of Search ..................... 514/12, 44; 530/350; 424/190.1; 435/252.3, 252.5, 410, 440, 91.4, 468, 471, 476, 480; 536/23.7, 23.71, 23.1

(56) References Cited

U.S. PATENT DOCUMENTS

| | | | |
|---|---|---|---|
| 5,045,314 | A | 9/1991 | Bone et al. |
| 5,055,293 | A | 10/1991 | Aronson et al. |
| 5,906,818 | A | 5/1999 | Heins et al. |

FOREIGN PATENT DOCUMENTS

| | | |
|---|---|---|
| WO | WO 94/21795 | 9/1994 |
| WO | WO 96/10083 | 4/1996 |
| WO | WO 98/18932 | 5/1998 |
| WO | WO 99/57282 | 11/1999 |

OTHER PUBLICATIONS

Carneiro et al., "Nematicidal Activity of *Bacillus* spp. Strains on Juveniles of *Meloidogyne javanica,* " *Nematological brasileira* (1998), pp. 12–21, vol. 22(1).

Favret et al., "Insecticidal Activity of *Bacillus laterosporus,* " *J. Invert. Path.* (1985), pp. 195–203, vol. 45.

Montaldi et al. "Parasporal Bodies of *Bacillus* laterosporus Sporangia, " J. Bac. (1990), pp. 2168–2171, vol. 172.

Orlova et al., "Insecticidal Activity of *Bacillus laterosporus,* " *Appl. Env. Micro.* (1998), pp. 2723–2725, vol. 64(7).

*Primary Examiner*—Christopher S. F. Low
*Assistant Examiner*—Chih-Min Kam
(74) *Attorney, Agent, or Firm*—Saliwanchik, Lloyd & Saliwanchik

(57) ABSTRACT

Disclosed and claimed are novel toxins and genes obtainable from *Bacillus laterosporus* isolates disclosed herein. In preferred embodiments, the subject genes and toxins are used to control Western corn rootworm.

6 Claims, No Drawings

PESTICIDAL TOXINS AND GENES FROM *BACILLUS LATEROSPORUS* STRAINS

CROSS-REFERENCE TO RELATED APPLICATIONS

The subject application is a continuation of Ser. No. 09/371,913 (filed Aug. 10, 1999) now U.S. Pat. No. 6,297, 369; which claims priority to Ser. No. 60/095,955 (filed Aug. 10, 1998) and to Ser. No. 60/138,251 (filed Jun. 8, 1999).

BACKGROUND OF THE INVENTION

Insects and other pests cost farmers billions of dollars annually in crop losses and in the expense of keeping these pests under control. The losses caused by insect pests in agricultural production environments include decrease in crop yield, reduced crop quality, and increased harvesting costs.

The corn rootworm (a coleopteran insect pest) is a serious plant pest. Extensive damage occurs to the United States corn crop each year due to root feeding by larvae of corn rootworm (Diabrotica spp.). It has been estimated that approximately 9.3 million acres of U.S. corn are infested with corn rootworm species complex each year. The corn rootworm species complex includes the Western corn rootworm (*Diabrotica virgifera virgifera*), Northern corn rootworm (*Diabrotica barberi*), and Southern corn rootworm (*Diabrotica undecimpunctata howardi*).

The life cycle of each Diabrotica species is similar. The eggs of the corn rootworm are deposited in the soil. Newly hatched larvae (the first instar) remain in the ground and feed on the smaller branching corn roots. Later instars of Western and Northern corn rootworms invade the inner root tissues that transport water and mineral elements to the plants. In most instances, larvae migrate to feed on the newest root growth. Tunneling into roots by the larvae results in damage which can be observed as brown, elongated scars on the root surface, tunneling within the roots, or varying degrees of pruning. Plants with pruned roots usually dislodge after storms that are accompanied by heavy rains and high winds. The larvae of Southern corn rootworm feed on the roots in a similar manner as the Western and Northern corn rootworm larvae. Southern corn rootworm larvae may also feed on the growing point of the stalk while it is still near the soil line, which may cause the plant to wilt and die.

After feeding for about 3 weeks, the corn rootworm larvae leave the roots and pupate in the soil. The adult beetles emerge from the soil and may feed on corn pollen and many other types of pollen, as well as on corn silks. Feeding on green silks can reduce pollination level, resulting in poor grain set and poor yield. The Western corn rootworm adult also feeds upon corn leaves, which can slow plant growth and, on rare occasions, kill plants of some corn varieties.

The soil-dwelling larvae of these Diabrotica species feed on the root of the corn plant, causing lodging. Lodging eventually reduces corn yield and often results in death of the plant. By feeding on cornsilks, the adult beetles reduce pollination and, therefore, detrimentally effect the yield of corn per plant. In addition, adults and larvae of the genus Diabrotica attack cucurbit crops (cucumbers, melons, squash, etc.) and many vegetable and field crops in commercial production as well as those being grown in home gardens.

It has been estimated that the annual cost of insecticides to control corn rootworm and the annual crop losses caused by corn rootworm damage exceeds a total of $1 billion in the United States each year (Meycalf, R. L. [1986] in *Methods for the Study of Pest Diabrotica*, Drysan, J. L. and T. A. Miller [Eds.], Springer-Verlag, New York, N.Y., pp. vii–xv). Approximately $250 million worth of insecticides are applied annually to control corn rootworms in the United States. In the Midwest, $60 million and $40 million worth of insecticide were applied in Iowa and Nebraska, respectively, in 1990. Even with insecticide use, rootworms cause about $750 million worth of crop damage each year, making them the most serious corn insect pest in the Midwest.

Control of corn rootworm has been partially addressed by cultivation methods, such as crop rotation and the application of high nitrogen levels to stimulate the growth of an adventitious root system. However, chemical insecticides are relied upon most heavily to guarantee the desired level of control. Insecticides are either banded onto or incorporated into the soil. Economic demands on the utilization of farmland restrict the use of crop rotation. In addition, an emerging two-year diapause (or overwintering) trait of Northern corn rootworms is disrupting crop rotations in some areas.

The use of insecticides to control corn rootworm also has several drawbacks. Continual use of insecticides has allowed resistant insects to evolve. Situations such as extremely high populations of larvae, heavy rains, and improper calibration of insecticide application equipment can result in poor control. Insecticide use often raises environmental concerns such as contamination of soil and of both surface and underground water supplies. The public has also become concerned about the amount of residual chemicals which might be found on food. Working with insecticides may also pose hazards to the persons applying them. Therefore, synthetic chemical pesticides are being increasingly scrutinized, and correctly so, for their potential toxic environmental consequences. Examples of widely used synthetic chemical pesticides include the organochlorines, e.g., DDT, mirex, kepone, lindane, aldrin, chlordane, aldicarb, and dieldrin; the organophosphates, e.g., chlorpyrifos, parathion, malathion, and diazinon; and carbamates. Stringent new restrictions on the use of pesticides and the elimination of some effective pesticides from the market place could limit economical and effective options for controlling costly pests.

Because of the problems associated with the use of organic synthetic chemical pesticides, there exists a clear need to limit the use of these agents and a need to identify alternative control agents. The replacement of synthetic chemical pesticides, or combination of these agents with biological pesticides, could reduce the levels of toxic chemicals in the environment.

A biological pesticidal agent that is enjoying increasing popularity is the soil microbe *Bacillus thuringiensis* (B.t.). The soil microbe *Bacillus thuringiensis* (B.t.) is a Gram-positive, spore-forming bacterium. Most strains of B.t. do not exhibit pesticidal activity. Some B.t. strains produce, and can be characterized by, parasporal crystalline protein inclusions. These "δ-endotoxins," which typically have specific pesticidal activity, are different from exotoxins, which have a non-specific host range. These inclusions often appear microscopically as distinctively shaped crystals. The proteins can be highly toxic to pests and specific in their toxic activity. Certain B.t. toxin genes have been isolated and sequenced. The cloning and expression of a B.t. crystal protein gene in *Escherichia coli* was described in the published literature more than 15 years ago (Schnepf, H. E., H. R. Whiteley [1981] *Proc. Natl. Acad. Sci. USA* 78:2893–2897). In addition, with the use of genetic engineering techniques, new approaches for delivering B.t. toxins to agricultural environments are under development, including the use of plants genetically engineered with B.t. toxin genes for insect resistance and the use of stabilized intact microbial cells as B.t. toxin delivery vehicles (Gaertner, F. H., L. Kim [1988] *TIBTECH* 6:S4–S7). Thus, isolated B.t. endotoxin genes are becoming commercially valuable.

Until the last fifteen years, commercial use of B.t. pesticides has been largely restricted to a narrow range of lepidopteran (caterpillar) pests. Preparations of the spores and crystals of *B. thuringiensis* subsp. kurstaki have been used for many years as commercial insecticides for lepidopteran pests. For example, *B. thuringiensis* var. kurstaki HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely israelensis and morrisoni (a.k.a. tenebrionis, a.k.a. B.t. M-7), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.). See also Couch, T. L. (1980) "Mosquito Pathogenicity of Bacillus thuringiensis var. israelensis," *Developments in Industrial Microbiology* 22:61–76; and Beegle, C. C. (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508 describe *Bacillus thuringiensis* var. tenebrionis, which is reportedly active against two beetles in the order Coleoptera. These are the Colorado potato beetle, *Leptinotarsa decemlineata*, and *Agelastica alni*.

Recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B.t. crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson, J. S., J. Payne, L. Kim [1992] *Bio/Technology* 10:271–275). CryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol* 62(1):80–86) and Shevelev et al. ([1993] *FEBS Lett.* 336:79–82) describe the characterization of Cry9 toxins active against lepidopterans. Published PCT applications WO 94/05771 and WO 94/24264 also describe B.t. isolates active against lepidopteran pests. Gleave et al. ([1991] *JGM* 138:55–62) and Smulevitch et al. ([1991] *FEBS Lett.* 293:25–26) also describe B.t. toxins. A number of other classes of B.t. genes have now been identified.

The 1989 nomenclature and classification scheme of H8fte and Whiteley for crystal proteins was based on both the deduced amino acid sequence and the host range of the toxin. That system was adapted to cover 14 different types of toxin genes which were divided into five major classes. The number of sequenced *Bacillus thuringiensis* crystal protein genes currently stands at more than fifty. A revised nomenclature scheme has been proposed which is based solely on amino acid identity (Crickmore et al. [1996] Society for Invertebrate Pathology, 29th Annual Meeting, IIIrd International Colloquium on *Bacillus thuringiensis*, University of Cordoba, Cordoba, Spain, Sep. 1–6, 1996, abstract). The mnemonic "cry" has been retained for all of the toxin genes except cytA and cytB, which remain a separate class. Roman numerals have been exchanged for Arabic numerals in the primary rank, and the parentheses in the tertiary rank have been removed. Many of the original names have been retained, with the noted exceptions, although a number have been reclassified. See also "Revisions of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean, *Microbiology and Molecular Biology Reviews* (1998) Vol. 62:807–813; and Crickmore, Zeigler, Feitelson, Schnepf, Van Rie, Lereclus, Baum, and Dean, "*Bacillus thuringiensis* toxin nomenclature" (1999) available on Dr. Neil Crickmore's website of the University of Sussex at Brighton. That system uses the freely available software applications CLUSTAL W and PHYLIP. The NEIGHBOR application within the PHYLIP package uses an arithmetic averages (UPGMA) algorithm.

As a result of extensive research and investment of resources, other patents have issued for new B.t. isolates and new uses of B.t. isolates. See Feitelson et al., supra, for a review. However, the discovery of new B.t. isolates and new uses of known B.t. isolates remains an empirical, unpredictable art.

Favret and Yousten ([1985] *J. Invert. Path.* 45:195–203) tested the insecticidal activity of *Bacillus laterosporus* strains, but concluded that the low levels of toxicity demonstrated by those strains indicate that those strains were not potential candidates for biocontrol agents. Montaldi and Roth (172 *J. Bac.* 4; April 1990; pp.2168–2171) conducted electron microscopy examination parasporal bodies of *Bacillus laterosporus* sporangia. Bone et al. (U.S. Pat. No. 5,045,314) report that the spores of selected strains of *B. laterosporus* inhibit egg hatching and/or larval development of an animal-parasitic nematode. Aronson et al. (U.S. Pat. No. 5,055,293) describe a spore-forming *Bacillus laterosporus* designated P5 (ATCC 53694). *Bacillus laterosporus* NRS-590 is used therein as a negative control. Aronson et al. postulate that B.l. P5 can either invade very young corn rootworm larvae for immediate or later damage or that it blocks the receipt or response of the rootworm to the corn root signal that directs it to the roots. WO 94/21795 and WO 96/10083 describe toxins that are purportedly active against certain pests. WO 98/18932 describes many new classes of microbial toxins that are active against various types of insects. Various probes and primers are also disclosed therein. Orlova et al. (64 *Appl. Env. Micro.* 7, July 1998, pp.2723–2725) report that the crystalline inclusions of certain strains of *Bacillus laterosporus* might potentially be used as candidates for mosquito control.

Obstacles to the successful agricultural use of B.t. toxins include the development of resistance to B.t. toxins by insects. In addition, certain insects can be refractory to the effects of B.t. The latter includes insects such as boll weevil and black cutworm as well as adult insects of most species which heretofore have demonstrated no apparent significant sensitivity to B.t. δ-endotoxins. While resistance management strategies in B.t. transgene plant technology have become of great interest, there remains a great need for developing genes that can be successfully expressed at adequate levels in plants in a manner that will result in the effective control of various insects.

BRIEF SUMMARY OF THE INVENTION

The subject invention concerns materials and methods useful in the control of non-mammalian pests and, particularly, plant pests. In one embodiment, the subject invention provides novel, pesticidal toxins and toxin-encoding genes that are obtainable from *Bacillus laterosporus* isolates. In a preferred embodiment, the target pests are corn rootworm pests. The toxins of the subject invention include heat-labile, soluble toxins which can be obtained from the supernatant of cultures of the subject *Bacillus laterosporus* strains. The toxins of the subject invention also include smaller, heat-labile toxins obtainable from these strains.

The subject invention further provides nucleotide sequences which encode the toxins of the subject invention. The nucleotide sequences of the subject invention encode toxins which are distinct from previously-described toxins. The nucleotide sequences of the subject invention can also be used in the identification and characterization of genes which encode pesticidal toxins.

In one embodiment of the subject invention, the subject Bacillus isolates can be cultivated under conditions resulting in high multiplication of the microbe. After treating the microbes to provide single-stranded genomic nucleic acid, the DNA is characterized using nucleotide sequences according to the subject invention. Characteristic fragments of toxin-encoding genes will be amplified by the procedure, thus identifying the presence of the toxin-encoding gene(s).

In a preferred embodiment, the subject invention concerns plants and plant cells transformed to produce at least one of the pesticidal toxins of the subject invention such that the transformed plant cells express pesticidal toxins in tissues consumed by target pests. In addition, mixtures and/or combinations of toxins can be used according to the subject invention.

Transformation of plants with the genetic constructs disclosed herein can be accomplished using techniques well known to those skilled in the art and would typically involve modification of the gene to optimize expression of the toxin in plants.

BRIEF DESCRIPTION OF THE SEQUENCES

Nucleotide sequences of the subject invention encode toxins which are distinct from previously-described toxins. Other nucleotide sequences of the subject invention can also be used in diagnostic and analytic procedures that are well known in the art. For example, the probes, primers, and partial sequences can be used for identifying and characterizing genes which encode pesticidal toxins.

In one embodiment of the subject invention, the subject Bacillus isolates can be cultivated under conditions resulting in high multiplication of the microbe. After treating the microbes to provide single-stranded genomic nucleic acid, the DNA is characterized using nucleotide sequences according to the subject invention. Characteristic fragments of toxin-encoding genes will be amplified by the procedure, thus identifying the presence of the toxin-encoding gene(s).

In a preferred embodiment, the subject invention concerns plant cells transformed to produce at least one of the pesticidal toxins of the subject invention such that the transformed plant cells express pesticidal toxins in tissues consumed by target pests. In addition, mixtures and/or combinations of toxins can be used according to the subject invention. In some preferred embodiments, a MIS toxin and a WAR toxin are used together.

Transformation of plants with the genetic constructs disclosed herein can be accomplished using techniques well known to those skilled in the art and would typically involve modification of the gene to optimize expression of the toxin in plants.

Isolates useful according to the subject invention will be deposited in the permanent collection of the Agricultural Research Service Patent Culture Collection (NRRL), Northern Regional Research Center, 1815 North University Street, Peoria, Ill. 61604, USA. The culture repository numbers are as follows:

```
SEQ ID NO:1 is a MIS probe.
SEQ ID NO:2 is a WAR probe.
SEQ ID NO:3 is a MIS-forward primer.
SEQ ID NO:4 is a MIS-reverse primer.
SEQ ID NO:5 is a nucleotide sequence from the MIS toxin gene from B.l. strain MB438.
SEQ ID NO:6 is the nucleotide sequence of the MIS toxin gene from B.l. strain MB438.
SEQ ID NO:7 is the polypeptide sequence of the MIS toxin from B.l. strain MB438.
SEQ ID NO:8 is the nucleotide sequence of the WAR toxin gene from B.l. strain MB438.
SEQ ID NO:9 is the polypeptide sequence of the WAR toxin from B.l. strain MB438.
SEQ ID NO:10 is a nucleotide sequence from the MIS toxin from B.l. strain MB439.
```

DETAILED DISCLOSURE OF THE INVENTION

The subject invention concerns materials and methods useful in the control of non-mammalian pests and, particularly, plant pests. In one embodiment, the subject invention provides novel, pesticidal toxins and toxin-encoding genes that are obtainable from *Bacillus laterosporus* (B.l.) isolates. In a preferred embodiment, the target pests are corn rootworm pests. The toxins of the subject invention include heat-labile, soluble toxins which can be obtained from the supernatant of cultures of the subject *Bacillus laterosporus* strains. MIS- and WAR-type toxins obtainable from these strains are described in detail, below. The toxins of the subject invention also include smaller, heat-labile toxins obtainable from these strains.

The subject invention further provides nucleotide sequences which encode the toxins of the subject invention.

| Culture | Repository No. | Deposit Date |
|---|---|---|
| B.l. MB438 | NRRL B-30085 | December 21, 1998 |
| B.l. MB439 | NRRL B-30086 | December 21, 1998 |
| E. coli MR957 (MB438 clone) | NRRL B-30048 | August 14, 1998 |
| B.t. PS177C8 | NRRL B-21867 | October 24, 1997 |

Cultures which have been deposited for the purposes of this patent application were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

Mutants of the isolates referred to herein can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

In one embodiment, the subject invention concerns materials and methods including nucleotide primers and probes for isolating, characterizing, and identifying Bacillus genes encoding protein toxins which are active against nonmammalian pests. The nucleotide sequences described herein can also be used to identify new pesticidal Bacillus isolates. The invention further concerns the genes, isolates, and toxins identified using the methods and materials disclosed herein.

The new toxins and polynucleotide sequences provided here are defined according to several parameters. One characteristic of the toxins described herein is pesticidal activity. In a specific embodiment, these toxins have activity against Western corn rootworm. The toxins and genes of the subject invention can be further defined by their amino acid and nucleotide sequences. The sequences of the molecules can be defined in terms of homology to certain exemplified sequences as well as in terms of the ability to hybridize with, or be amplified by, certain exemplified probes and primers.

In a preferred embodiment, the MIS-type of toxins of the subject invention have a molecular weight of about 70 to about 100 kDa and, most preferably, the toxins have a size of about 80 kDa. Typically, these toxins are soluble and can be obtained from the supernatant of Bacillus cultures as described herein. These toxins have toxicity against nonmammalian pests. In a preferred embodiment, these toxins have activity against Western corn rootworm. The MIS proteins are further useful due to their ability to form pores in cells. These proteins can be used with second entities including, for example, other proteins. When used with a second entity, the MIS protein will facilitate entry of the second agent into a target cell. In a preferred embodiment, the MIS protein interacts with MIS receptors in a target cell and causes pore formation in the target cell. The second entity may be a toxin or another molecule whose entry into the cell is desired.

The subject invention further concerns WAR-type of toxins having a size of about 30–50 kDa and, most typically, have a size of about 40 kDa. Typically, these toxins are soluble and can be obtained from the supernatant of Bacillus cultures as described herein.

The MIS- and WAR-type of toxins of the subject invention can be identified with primers described herein.

Another unique type of toxin has been identified as being produced by the Bacillus strains of the subject invention. These toxins are much smaller than the MIS- and WAR-type of toxins of the subject invention. These toxins, like the MIS- and WAR-type of toxins, are heat labile. However, these toxins are in the approximate size range of about 10 kDa to about 1 kDa. These toxins are also soluble and can be obtained from the supernatants of Bacillus cultures as described herein.

With the teachings provided herein, one skilled in the art could readily produce and use the various toxins and polynucleotide sequences described herein.

Genes and Toxins. As used herein, the terms "wild-type toxin" and "wild-type gene" refer to the genes and toxins naturally produced by the subject isolates (MB438 and MB439). The genes and toxins of the subject invention include not only the full length, wild-type sequences but also fragments of these sequences, variants, mutants, and fusion proteins which retain the characteristic pesticidal activity of the toxins specifically exemplified herein. For example, U.S. Pat. No. 5,605,793 describes methods for generating additional molecular diversity by using DNA reassembly after random fragmentation. Moreover, internal deletions can be made to the genes and toxins specifically exemplified herein, so long as the modified toxins retain pesticidal activity. Chimeric genes and toxins, produced by combining portions from more than one Bacillus toxin or gene, may also be utilized according to the teachings of the subject invention. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It is apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from Bacillus isolates and/or DNA libraries using the teachings provided herein. There are a number of methods for obtaining the pesticidal toxins of the instant invention. For example, antibodies to the pesticidal toxins disclosed and claimed herein can be used to identify and isolate toxins from a mixture of proteins. Specifically, antibodies may be raised to the portions of the toxins which are most constant and most distinct from other Bacillus toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins are within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. Probes provide a rapid method for identifying toxin-encoding genes of the subject invention. The nucleotide segments which are used as probes according to the invention can be synthesized using a DNA synthesizer and standard procedures.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid identity will typically be greater than 60%, preferably be greater than 75%, more preferably greater than 80%, more preferably greater than 90%, and can be greater than 95%. These identities are as determined using standard alignment techniques, preferably those used by Crickmore et al. as discussed in the Background section of the subject Specification. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Listed below in Table 1 are examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |

TABLE 1-continued

| Class of Amino Acid | Examples of Amino Acids |
|---|---|
| Acidic | Asp, Glu |
| Basic | Lys, Arg, His |

In some instances, non-conservative substitutions can also be made. The critical factor is that these substitutions must not significantly detract from the biological activity of the toxin.

As used herein, reference to "isolated" polynucleotides and/or "purified" toxins refers to these molecules when they are not associated with the other molecules with which they would be found in nature. Thus, reference to "isolated and purified" signifies the involvement of the "hand of man" as described herein. Chimeric toxins and genes also involve the "hand of man."

Recombinant Hosts. The toxin-encoding genes of the subject invention can be introduced into a wide variety of microbial or plant hosts. Expression of the toxin gene results, directly or indirectly, in the production and maintenance of the pesticide. The transformation of plant hosts is preferred. Pests that feed on the recombinant plant which expresses the toxin will thereby contact the toxin. With suitable microbial hosts, e.g., Pseudomonas, the microbes can be applied to the situs of the pest, where they will proliferate and be ingested. With any of the various approaches, the result is control of the pest. Alternatively, the microbe hosting the toxin gene can be killed and treated under conditions that prolong the activity of the toxin and stabilize the cell. The treated cell, which retains the toxic activity, then can be applied to the environment of the target pest. The Bacillus toxin can also be applied by introducing a gene via a suitable vector into a microbial host and then applying the host to the environment in a living state A wide variety of ways are available for introducing a Bacillus gene encoding a toxin into a host under conditions which allow for stable maintenance and expression of the gene. These methods are well known to those skilled in the art and are described, for example, in U.S. Pat. No. 5,135,867, which is incorporated herein by reference.

Synthetic genes which are functionally equivalent to the toxins of the subject invention can also be used to transform hosts. Methods for the production of synthetic genes can be found in, for example, U.S. Pat. No. 5,380,831. In preferred embodiments, the genes of the subject invention are optimized for expression in plants.

Treatment of Cells. As mentioned above, Bacillus or recombinant cells expressing a Bacillus toxin can be treated to prolong the toxin activity and stabilize the cell. The pesticide microcapsule that is formed comprises the Bacillus toxin within a cellular structure that has been stabilized and will protect the toxin when the microcapsule is applied to the environment of the target pest. Suitable host cells may include either prokaryotes or eukaryotes. As hosts, of particular interest will be the prokaryotes and the lower eukaryotes, such as fungi. The cell will usually be intact and be substantially in the proliferative form when treated, rather than in a spore form.

Treatment of the microbial cell, e.g., a microbe containing the Bacillus toxin gene, can be by chemical or physical means, or by a combination of chemical and/or physical means, so long as the technique does not deleteriously affect the properties of the toxin, nor diminish the cellular capability of protecting the toxin. Methods for treatment of microbial cells are disclosed in U.S. Pat. Nos. 4,695,455 and 4,695,462, which are incorporated herein by reference.

Methods and Formulations for Control of Pests. Control of pests using the toxins, and genes of the subject invention can be accomplished by a variety of methods known to those skilled in the art. These methods include, for example, the application of Bacillus isolates to the pests (or their location), the application of recombinant microbes to the pests (or their locations), and the transformation of plants with genes which encode the pesticidal toxins of the subject invention. Transformations can be made by those skilled in the art using standard techniques. Materials necessary for these transformations are disclosed herein or are otherwise readily available to the skilled artisan.

Formulated bait granules containing an attractant and the toxins of the Bacillus isolates, or recombinant microbes comprising the genes obtainable from the Bacillus isolates disclosed herein, can be applied to the soil. Formulated product can also be applied as a seed-coating or root treatment or total plant treatment at later stages of the crop cycle. Plant and soil treatments of Bacillus cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include Theological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations that contain cells will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Polynucleotide Probes. It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The probes may be RNA, DNA, or PNA (peptide nucleic acid). The probe will normally have at least about 10 bases, more usually at least about 17 bases, and may have up to about 100 bases or more. Longer probes can readily be utilized, and such probes can be, for example, several kilobases in length. The probe sequence is designed to be at least substantially complementary to a portion of a gene encoding a toxin of interest. The probe need not have perfect complementarity to the sequence to which it hybridizes. The probes may be labeled utilizing techniques which are well known to those skilled in this art.

One approach for the use of the subject invention as probes entails first identifying by Southern blot analysis of a gene bank of the Bacillus isolate all DNA segments homologous with the disclosed nucleotide sequences. Thus, it is possible, without the aid of biological analysis, to know in advance the probable activity of many new Bacillus isolates, and of the individual gene products expressed by a given Bacillus isolate. Such a probe analysis provides a rapid method for identifying potentially commercially valuable insecticidal toxin genes within the multifarious subspecies of Bacillus.

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane.

The particular hybridization technique is not essential to the subject invention. As improvements are made in hybridization techniques, they can be readily applied.

The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

In the use of the nucleotide segments as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169–170. This information is hereby incorporated by reference.

As used herein "moderate to high stringency" conditions for hybridization refers to conditions which achieve the same, or about the same, degree of specificity of hybridization as the conditions employed by the current applicants. Examples of moderate and high stringency conditions are provided herein. Specifically, hybridization of immobilized DNA on Southern blots with 32P-labeled gene-specific probes was performed by standard methods (Maniatis et al.). In general, hybridization and subsequent washes were carried out under moderate to high stringency conditions that allowed for detection of target sequences with homology to the exemplified toxin genes. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285).

$$Tm=81.5° C.+16.6Log[Na+]+0.41(\%G+C)-0.61(\%formamide)-600/length \text{ of duplex in base pairs.}$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

$$Tm(° C.)=2(\text{number T/A base pairs})+4(\text{number G/C base pairs})$$

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683–693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

| Low: | 1 or 2X SSPE, room temperature |
| Low: | 1 or 2X SSPE, 42° C. |
| Moderate: | 0.2X or 1X SSPE, 65° C. |
| High: | 0.1X SSPE, 65° C. |

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant probe to function in the same capacity as the original probe. Preferably, this homology is greater than 50%; more preferably, this homology is greater than 75%; and most preferably, this homology is greater than 90%. The degree of homology or identity needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR Technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Ambeim [1985] "Enzymatic Amplification of β-Globin Genomic Sequences and Restriction Site Analysis for Diagnosis of Sickle Cell Anemia," *Science* 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan.

All of the references cited herein are hereby incorporated by reference.

Following are examples which illustrate procedures for practicing the invention. These examples should not be construed as limiting. All percentages are by weight and all solvent mixture proportions are by volume unless otherwise noted.

EXAMPLE 1

Culturing of *Bacillus laterosporus* Isolates Useful According to the Invention

Native *Bacillus latersporous* strains and B.t. recombinants expressing B.l. MIS and WAR toxins were cultured in TB (+glycerol) liquid medium at 30° C. and 300 RPM for 25 hours. Cells were pelleted by centrifugation and supernatants ("SN") decanted and saved. EDTA was added to 1 mM and samples stored at −20° C. Fresh samples were used for bioassays on the same day as harvesting. Frozen samples were thawed at 4° C. and centrifuged to pellet and eliminate any solids and were then presented to then used for bioassay or fractionation.

EXAMPLE 2

Preparation of Genomic DNA and Southern Blot Analysis

Total cellular DNA was prepared from various *Bacillus laterosporus* strains grown to an optical density of 0.5–0.8 at 600 nm visible light in Luria Bertani (LB) broth. DNA was extracted using the Qiagen Genomic-tip 500/G kit or Genomic-Tip 20/G and Genomic DNA Buffer Set according to protocol for Gram positive bacteria (Qiagen Inc.; Valencia, Calif.). Prepared total genomic DNA was digested with various restriction enzymes, electrophoresed on a 0.8% agarose gel, and immobilized on a supported nylon membrane using standard methods (Maniatis, T., E. F. Fritsch, J. Sambrook [1982] *Molecular Cloning: A Laboratory Manual*, Cold Spring Harbor Laboratory, Cold Spring Harbor, N.Y.). Novel toxin genes were detected using $^{32}$P-labeled probes in standard Southern hybridizations or by non-radioactive methods using the DIG nucleic acid labeling and detection system (Boehringer Mannheim; Indianapolis, Ind.).

The approximately 2.6 kbp, MIS probe is shown in SEQ ID NO:1. The approximately 1.3 kbp WAR probe is shown in SEQ ID NO:2. These probes can be prepared in various ways including the use of a "gene machine," or they can be cloned from B.t. isolate PS177C8 and PCR amplified with primers homologous to the 5' and 3' ends of each respective gene. In the latter case, DNA fragments were gel purified and approximately 25 ng of each DNA fragment was randomly labeled with $^{32}$P for radioactive detection. Approximately 300 ng of each DNA fragment was randomly labeled with the DIG High Prime kit for nonradioactive detection. Hybridization of immobilized DNA with randomly $^{32}$P-labeled probes were performed in standard formamide conditions: 50% formamide, 5×SSPE, 5×Denhardt's solution, 2% SDS, 0.1 mg/ml at 42° C. overnight. Blots were washed under low stringency in 2×SSC, 0.1% SDS at 42° C. and exposed to film.

Shown below in Table 2 are the results of restriction fragment length polymorphism (RFLP) of total cellular DNA from *Bacillus laterosporus* strains MB438 and MB439 as determined by Southern blot analysis probed with either MIS or WAR probes, as indicated. Bands contain at least a fragment of the MIS- or WAR-like operon of interest.

TABLE 2

| RFLP Class | Strain Name | MIS probe Hybridization bands | WAR probe Hybridization bands |
|---|---|---|---|
| A | MB438 | HindIII: 8,414; 7,871<br>XbaI: 12,972; 8,138 | HindIII: 7,781, 7,364, 2,269<br>XbaI: 12,792, 7,871 |
| B | MB439 | HindIII: 7,871<br>XbaI: 12,972 | HindIII: 7,364, 2,269<br>XbaI: 12,792 |

EXAMPLE 3

Toxin Gene Cloning

Lambda libraries of total genomic DNA from *Bacillus laterosporus* strains MB439 or MB438 were prepared from partially digested, size fractionated DNA in the size range of 9–20 kb. Specific digestion times using 1:10 diluted NdeII enzyme (approximately 0.5 units) were determined to optimize desired size range of digested DNA. DNA was digested for the appropriate time and then fractionated on a 0.7% agarose gel. DNA was visualized using ethidium bromide staining and DNA within the size range of 9–20 kb was excised from the gel. The gel fragment was put into dialysis tubing (12–14,000 MW cutoff) along with 2 ml of 10 mM Tris-HCl, 1 mM EDTA buffer, pH 8.0 (TE). DNA was electroeluted from the gel fragment in 0.1×TAE buffer at approximately 30 mA for one hour. DNA was removed from tubing in the TE buffer and purified using Elutip column and protocol (Schleicher and Schuell; Keene, N.H.). Purified DNA was ethanol precipitated and resuspended in 10 ul TE.

Purified, fractionated DNA was ligated into Lambda-GEM-11 BamHI digested arms (Promega Corp., Madison, Wis.) according to protocol. Ligated DNA was then packaged into lambda phage using Gigapack III Gold packaging extract (Stratagene Corp., La Jolla, Calif.) according to protocol. *E. coli* bacterial strain KW251 was infected with packaging extracts and plated onto LB plates in LB top agarose. Plaques were lifted onto nitrocellulose filters and prepared for hybridization using standard methods (Maniatis et al., supra). $^{32}$P-labeled probe (see above) was prepared and filters hybridized and washed as described above. Plaques containing the desired clone were visualized by exposing the filters to Kodak XAR-5 film. The plaques were isolated from the plates and phage resuspended from the agar into SM buffer. DNA from the phage was prepared using LambdaSorb phage adsorbent (Promega, Madison, Wis.). PCR was performed on the phage DNA to verify that it contained the target operon using SEQ ID NO:3 and SEQ ID NO:4 as primers. The PCR reactions yielded a 1 kb band in both DNA samples reaffirming that those clones contain the mis-type gene. To identify a smaller fragment of DNA containing the operon of interest which could then be subcloned into a bacterial vector for further analysis and expression, the phage DNAs were digested with various enzymes, fractionated on a 1% agarose gel and blotted for Southern analysis. Southern analysis was performed as described above. A HincII fragment approximately 10 kb in size was identified for MB438. This fragment was gel purified and cloned into the EcoRV site of pBluescriptII (SK+); the resulting plasmid is designated pMYC2608, and the recombinant *E.coli* strain containing this plasmid is designated MR957.

EXAMPLE 4

Sequencing of the MB438 MIS and WAR Genes

A partial DNA sequence for the MB438 mis gene was determined on a PCR-amplified DNA fragment. PCR using MIS primers (SEQ ID NO:3 and SEQ ID NO:4) was performed on total cellular genomic DNA from MB438 and MB439. MB438 yielded an approximately 1-kbp DNA fragment which was subsequently cloned into the PCR DNA TA-cloning plasmid vector, pCR2.1, as described by the supplier (Invitrogen, San Diego, Calif.). Plasmids were isolated from recombinant clones of the MB438 PCR and tested for the presence of an approximately 1-kbp insert by PCR using the plasmid vector primers, T3 and T7. Those that contained the insert were then isolated for use as sequencing templates using QIAGEN (Santa Clarita, Calif.) miniprep kits as described by the supplier. Sequencing reactions were performed using the Dye Terminator Cycle Sequencing Ready Reaction Kit from PE Applied Biosystems. Sequencing reactions were run on a ABI PRISM 377 Automated Sequencer. Sequence data was collected, edited, and assembled using the ABI PRISM 377 Collection, Factura, and AutoAssembler software from PE ABI. A partial nucleotide sequence of the MB438 mis-type gene is shown as SEQ ID NO:5.

Complete sequences for the MB438 MIS and WAR genes were determined by assembling sequence data from random restriction fragments from pMYC2608 and by primer walking the DNA insert in pMYC2608. Insert DNA from plasmid pMYC2608 was isolated by excision from the vector using polylinker restriction enzymes NotI and ApaI, fractionation on a 0.7% agarose gel and purification from the agarose gel using the QiaexII kit (Qiagen Inc.; Valencia, Calif.). Gel purified insert DNA was then digested with restriction enzymes AluI, MseI, and RsaI, and fractionated on a 1% agarose gel. DNA fragments between 0.5 and 1.5 kb were excised from the gel and purified using the QiaexII kit. Recovered fragments were ligated into EcoRV digested pBluescriptII and transformed into XL10Gold cells. Miniprep DNA was prepared from randomly chosen transformants, digested with NotI and ApaI to verify insert and used for sequencing. Sequencing reactions were performed using dRhodamine Sequencing kit (ABI Prism/Perkin Elmer Applied Biosystems). Sequences were run out on sequencing gel according to protocol (ABI Prism) and analyzed using Factura and Autoassembler programs (ABI Prism). The complete nucleotide sequence of the MB438 mis gene is shown as SEQ ID NO:6; the deduced MB438 MIS peptide sequence is shown as SEQ ID NO:7. The complete nucleotide sequence of the MB438 war gene is shown as SEQ ID NO:8; the deduced MB438 WAR peptide sequence is shown as SEQ ID NO:9.

A partial DNA sequence for the MB439 mis gene was determined from PCR-amplified DNA fragments. PCR using primers SEQ ID NO:3 and SEQ ID NO:4 was performed on total cellular genomic DNA from MB439. An approximately 1-kbp DNA fragment was obtained which was subsequently cloned into the PCR DNA TA-cloning plasmid vector, pCR-TOPO, as described by the supplier (Invitrogen, San Diego, Calif.). Plasmids were isolated from recombinant clones of the MB439 PCR and tested for the presence of an approximately 1-kpb insert by PCR using the plasmid vector primers, T3 and T7. Those that contained the insert were then isolated for use as sequencing templates using QIAGEN (Santa Clarita, Calif.) miniprep kits as described by the supplier. Sequencing reactions were performed using the Dye Terminator Cycle Sequencing Ready Reaction Kit from PE Applied Biosystems. Sequencing reactions were run on an ABI PRISM 377 Automated Sequencer. Sequence data was collected, edited, and assembled using the ABI PRISM 377 Collection, Factura, and AutoAssembler software from PE ABI. The partial nucleotide sequence of the MB439 mis gene is shown as SEQ ID NO:10.

EXAMPLE 5

Subcloning MB438 MIS and WAR Toxins for Expression in *Bacillus thuringiensis*

Expression of the MB438 MIS and WAR toxins in B.t. was achieved by subcloning the cloned genomic DNA fragment from pMYC2608 into a high copy number shuttle vector capable of replication in both *E. coli* and B.t. hosts. The shuttle vector, pMYC2614, is a modified version of pHT370 (O. Arantes and D. Lereclus. 1991. Gene 108:115–119), containing the multiple cloning site region of the pBluescript II (Stratagene). The genomic DNA insert containing the war and mis genes was excised from pMYC2608 using NotI and ApaI restriction enzymes, gel purified and ligated into the NotI and ApaI sites of pMYC2614. The resulting B.t. shuttle plasmid was designated pMYC2609.

To test the expression of the MB438 toxin genes in B.t., pMYC2609 was transformed into the acrystallierous (Cry-) B.t. host, CryB (A. Aronson, Purdue University, West Lafayette, Ind.), by electroporation. This recombinant strain was designated MR557. WAR toxin expression was demonstrated by immunoblotting with antibodies generated to the PS177C8 WAR toxin. Culture supernatant and cell pellet preparations from MR557 were assayed against western corn rootworm as described in Example 8 below.

EXAMPLE 6

Western Corn Rootworm Bioassays of MB438 and MB439

Supernatant samples prepared as discussed in Example 1 were top loaded on artificial diet at a rate of 215 $\mu$l/1.36 cm$^2$. These preparations were then infested with neonate Western corn rootworm and were held for 4 days in darkness at 25° C. Unless otherwise indicated, samples were evaluated for mortality on day 4 post-infestation.

Table 3 relates to time courses for MB438 and MB439. MB438 and MB439 demonstrate appearance of activity around 22–30 h (MB438) and 24–39 h (MB 439). All strains were grown on TBG medium. None of these samples were heat treated.

TABLE 3

| Strain | Hours | % | # Dead | Total |
|---|---|---|---|---|
| MB438 | 24 | 6% | 2 | 36 |
| MB438 | 26 | 6% | 2 | 35 |
| MB438 | 30 | 100% | 39 | 39 |
| MB438 | 32 | 100% | 41 | 41 |
| MB438 | 48 | 72% | 26 | 36 |
| MB438 | 16 | 21% | 6 | 29 |

TABLE 3-continued

| Strain | Hours | % | # Dead | Total |
|---|---|---|---|---|
| MB438 | 18 | 18% | 7 | 38 |
| MB438 | 22 | 92% | 35 | 38 |
| MB438 | 24 | 93% | 27 | 29 |
| MB438 | 39 | 100% | 28 | 28 |
| MB439 | 20 | 19% | 10 | 54 |
| MB439 | 24 | 76% | 26 | 34 |
| MB439 | 28 | 93% | 26 | 28 |
| MB439 | 44 | 100% | 28 | 28 |
| MB439 | 16 | 11% | 3 | 28 |
| MB439 | 18 | 8% | 3 | 36 |
| MB439 | 22 | 3% | 1 | 36 |
| MB439 | 24 | 14% | 4 | 28 |
| MB439 | 39 | 100% | 30 | 30 |

The results reported in Table 4 show that heating eliminates most or all of the activity present in fresh, unheated samples of 24 h and 48 h cultured MB438 and MB439.

TABLE 4

| Strain | Heated? | Hours | Medium | % Mortality | # Dead | Total |
|---|---|---|---|---|---|---|
| MB438 | NO | 24 | TBG | 88% | 36 | 41 |
| MB438 | YES | 24 | TBG | 22% | 11 | 49 |
| MB438 | NO | 24 | TBG | 91% | 29 | 32 |
| MB438 | YES | 24 | TBG | 6% | 2 | 35 |
| MB438 | NO | 24 | N/A | 78% | 25 | 32 |
| MB438 | YES | 24 | N/A | 23% | 6 | 26 |
| MB439 | NO | 24 | TBG | 71% | 30 | 42 |
| MB439 | YES | 24 | TBG | 16% | 7 | 45 |
| MB439 | NO | 24 | TBG | 93% | 40 | 43 |
| MB439 | YES | 24 | TBG | 17% | 4 | 24 |
| MB439 | NO | 24 | TBG | 100% | 50 | 50 |
| MB439 | YES | 24 | TBG | 19% | 8 | 43 |
| MB439 | NO | 48 | TBG | 98% | 47 | 48 |
| MB439 | YES | 48 | TBG | 20% | 7 | 35 |
| MB439 | NO | 24 | TBG | 83% | 45 | 54 |
| MB439 | YES | 24 | TBG | 4% | 2 | 52 |
| MB439 | NO | 48 | TBG | 85% | 41 | 48 |
| MB439 | YES | 48 | TBG | 12% | 6 | 51 |
| MB439 | NO | 24 | TBG | 91% | 43 | 47 |
| MB439 | YES | 24 | TBG | 11% | 5 | 47 |
| MB439 | NO | 48 | TBG | 97% | 30 | 31 |
| MB439 | YES | 48 | TBG | 16% | 7 | 44 |

The results reported in Table 5 show that the activity of MB438 and MB439 is dose-responsive. All of the strains were grown on TBG medium. None of the samples were heat treated. All of the samples are 24-hour cultures.

TABLE 5

| Strain | Dilution | % Mortality | # Dead | Total |
|---|---|---|---|---|
| MB438 | −20 C. - stored SN | 96% | 27 | 28 |
| MB438 | 0.25X | 93% | 25 | 27 |
| MB438 | 0.125X | 83% | 24 | 29 |
| MB438 | 0.0625X | 67% | 24 | 36 |
| MB438 | 0.03125X | 45% | 13 | 29 |
| MB439 | −20 C. - stored SN | 97% | 34 | 35 |
| MB439 | Whole SN diluted 0.25X | 83% | 24 | 29 |
| MB439 | Whole SN diluted 0.125X | 77% | 24 | 31 |
| MB439 | Whole SN diluted 0.0625X | 69% | 24 | 35 |
| MB439 | Whole SN diluted 0.03125X | 55% | 21 | 38 |

EXAMPLE 7

Western Corn Rootworm Bioassays of Fractionated Samples

For dialyzed samples, aliquots of culture supernatant were transferred to cellulosic dialysis tubing and were dialyzed against 25 mM $NaPO_4$, 1 mM EDTA, pH 7, with stirring overnight at 4° C. This eliminates any free-flowing components of the SN smaller than the nominal molecular weight cut off of the dialysis membrane. Pore sizes were 6–8 kD and 50 kD and these samples examine the activity of components retained within the dialysis membrane which may be referred to as "high molecular weight."

Low molecular weight fractions were generated by ultrafiltration ("UF") across either 1, 3, or 10 kD pore size membranes by nitrogen gas pressure at 4° C. This method results in solutions containing supernatant components smaller than the nominal molecular weight cut off of the UF membrane. These solutions are referred to as "permeates."

The results reported in Table 6 show that the less-than-10 kD component of MB438 and MB439 exhibits activity. All of the samples were grown on TBG medium. None of the samples were heat treated. All of the samples are 24-hour cultures.

TABLE 6

| Strain | Treatment | % Mortality | # Dead | Total |
|---|---|---|---|---|
| MB438 | MB438 4C-Stored SN | 92% | 24 | 26 |
| MB438 | MB438 UF Permeate, 10kD MWCO | 41% | 15 | 37 |
| MB439 | MB439 4C-Stored SN | 64% | 30 | 47 |
| MB439 | UF Permeate, 10kD MWCO | 52% | 17 | 33 |

The results reported in Table 7 show that the <10 kD components of MB438 and MB439 exhibit activity that is moderated by high heat, and that the elimination of the low molecular weight components upon dialysis does not eliminate activity. All samples were 24-hour cultures grown on TBG medium.

TABLE 7

| Strain | Heated? | Treatment | % Mortality | # Dead | Total |
|---|---|---|---|---|---|
| MB438 | NO | 4C-Stored SN | 97% | 30 | 31 |
| MB438 | NO | 10kD UF Permeate | 51% | 20 | 39 |
| MB438 | YES | 10kD UF Permeate Autoclaved | 16% | 6 | 38 |
| MB438 | NO | SN Dialyzed Overnight, 6–8kD | 94% | 45 | 48 |
| MB438 | NO | SN Dialyzed Overnight, 50kD | 84% | 37 | 44 |
| MB439 | NO | −20C-Stored SN | 98% | 40 | 41 |
| MB439 | NO | 10kD UF Permeate | 28% | 11 | 40 |
| MB439 | YES | 10kD UF Permeate Autoclaved | 16% | 5 | 31 |
| MB439 | NO | SN Dialyzed Overnight, 6–8kD | 76% | 35 | 46 |
| MB439 | NO | SN Dialyzed Overnight, 50kD | 55% | 22 | 40 |

The results reported in Table 8 show that MB438 and MB439 have activity in a less-than-10 kD component that does not pass through a 1kD UF membrane. All samples are 24-hour cultures grown on TBG medium.

TABLE 8

| Strain | Heated? | Treatment | % Mortality | # Dead | Total |
| --- | --- | --- | --- | --- | --- |
| MB438 | NO | −20C-Stored SN | 100% | 32 | 32 |
| MB438 | YES | −20C-Stored SN, Autoclaved | 57% | 20 | 35 |
| MB438 | NO | 10kD mwco UF Permeate | 78% | 25 | 32 |
| MB438 | YES | 10kD mwco UF Permeate, Autoclaved | 50% | 14 | 28 |
| MB438 | NO | 3kD mwco UF Permeate | 59% | 20 | 34 |
| MB438 | YES | 3kD mwco UF Permeate, Autoclaved | 45% | 14 | 31 |
| MB438 | NO | 1kD mwco UF Permeate | 31% | 23 | 75 |
| MB438 | YES | 1kD mwco UF Permeate, Autoclaved | 12% | 5 | 43 |
| MB439 | NO | −20C-Stored SN | 93% | 27 | 29 |
| MB439 | YES | −20C-Stored SN, Autoclaved | 34% | 12 | 35 |
| MB439 | NO | 10kD mwco UF Permeate | 62% | 21 | 34 |
| MB439 | YES | 10kD mwco UF Permeate, Autoclaved | 44% | 18 | 41 |
| MB439 | NO | 3kD mwco UF Permeate | 20% | 6 | 30 |
| MB439 | YES | 3kD mwco UF Permeate, Autoclaved | 33% | 10 | 30 |
| MB439 | NO | 1kD mwco UF Permeate | 20% | 16 | 82 |
| MB439 | YES | 1kD mwco UF Permeate, Autoclaved | 15% | 6 | 41 |

EXAMPLE 8

Bioactivity of of MR957 and MR557

Cultures of MR957 were grown in 5.0 ml of media (Difco TB premix; 4 g/liter of glycerol) in 16×150 mm plastic tubes with caps. Cultures were agitated on a rotating drum for 24 hours at 37° C. Cells were pelleted by centrifugation and supernatants decanted and saved. EDTA was added to 1 mM and samples stored at 20° C. For determination of cell density, samples were vortexed and 100 µl of each culture broth was transferred to a Falcon tube (14 mL; 17×100 mm). A 1:50 dilution was prepared by adding 4.9 mL distilled water to each tube and vortexed again. OD readings were made using a spectrophotometer at 600 nm. Recombinant B.t. strains were grown as described in Example 1.

Western corn rootworm bioassays for the *E. coli* clone MR957 and *B. thuringiensis* clone MR557 (each containing the MB438 mis and war genes) were done using essentially the same experimental design as described in Example 6. MR948 and MR539 are negative control strains containing cloning vectors without toxin gene inserts. For testing *E. coli* strains, supernatant or whole culture samples were applied to the surface of diet at a dose of 215 ul/1.36 $cm^2$, while cellular pellet samples were concentrated 5 fold and loaded onto diet at 50 ul/1.36 $cm^2$ (Table 9). For testing B.t. strains, supernatant samples were applied to the surface of diet at a dose of 215 ul/1.36 $cm^2$, while cellular pellet samples were concentrated 5 fold and loaded onto diet at various rates (Table 10). Approximately 6–8 larvae were transferred onto the diet immediately after the sample had evaporated. The bioassay plate was sealed with mylar sheeting using a tacking iron and pinholes were made above each well to provide gas exchange. Mortality was scored four days after investation.

The results for both of these tests demonstrate higher CRW mortality attributable to the cloned MB438 mis and war genes. Table 9 shows the qualitative activity of cloned MB438 toxins in crude *E. coli* culture preparations against western corn rootworm.

TABLE 9

| Clone | Toxins | Whole Culture | Supernatant | 5X Pellet |
|---|---|---|---|---|
| MR957 | MB438 MIS and WAR | 18 (146/824) | 15 (135/814) | 13 (110/832) |
| MR948 | None | 56 (468/827) | 54 (437/830) | 77 (618/812) |

Table 10 shows dose-dependent activity of cloned MB438 toxins in crude B.t. culture preparations against western corn rootworm. In Tables 9 and 10, the bold numbers are percent mortality; the numbers in parentheses indicate dead larvae divided by total larvae in the test.

TABLE 10

| Clone | Toxins | Supernatant 215 ul/1.36 $cm^2$ | Pellet 5X 200 ul/1.36 $cm^2$ | Pellet 5X ~200 ul/1.36 $cm^2$ | Pellet 5X 50 ul/1.36 $cm^2$ |
|---|---|---|---|---|---|
| MR557 | MB438 MIS and WAR | 94 (45/48) | 92 (35/38) | 47 (20/43) | 34 (19/56) |
| MR539 | None | 33 (15/45) | 35 (17/49) | 21 (11/53) | 7 (4/59) |

EXAMPLE 9

Insertion of Toxin Genes into Plants

One aspect of the subject invention is the transformation of plants with genes encoding the insecticidal toxin of the present invention. The transformed plants are resistant to attack by the target pest.

Genes encoding pesticidal toxins, as disclosed herein, can be inserted into plant cells using a variety of techniques which are well known in the art. Those techniques include transformation with T-DNA using *Agrobacterium tumefaciens* or *Agrobacterium rhizogenes* as transformation agent, fusion, injection, biolistics (microparticle bombardment), or electroporation as well as other possible methods.

If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA.

No special demands are made of the plasmids in the case of injection and electroporation. It is possible to use ordinary plasmids, such as, for example, pUC derivatives. In biolistic transformation, plasmid DNA or linear DNA can be employed.

A large number of cloning vectors comprising a replication system in *E. coli* and a marker that permits selection of the transformed cells are available for preparation for the insertion of foreign genes into higher plants. The vectors comprise, for example, pBR322, pUC series, M13 mp series, pACYC 184, etc. Accordingly, the sequence encoding the Bacillus toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

The transformed cells are regenerated into morphologically normal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants can be transformed with genes wherein the codon usage has been optimized for plants. See, for example, U.S. Pat. No. 5,380,831.

It should be understood that the examples and embodiments described herein are for illustrative purposes only and that various modifications or changes in light thereof will be suggested to persons skilled in the art and are to be included within the spirit and purview of this application and the following claims.

What is claimed is:

1. An isolated protein that has toxin activity against a corn rootworm pest, which comprises a polypeptide selected from the group consisting of
   a. an amino acid sequence that has at least 90% identity with SEQ ID NO:9 and retains the toxin activity of the polypeptide defined by SEQ ID NO:9;
   b. the amino acid sequence of SEQ ID NO:9 or a segment thereof that retains the toxin activity of the polypeptide defined by SEQ ID NO:9;
   c. an amino acid sequence that has at least 90% identity with SEQ ID NO:7 and retains the toxin activity of the polypeptide defined by SEQ ID NO:7; and
   d. the amino acid sequence of SEQ ID NO:7 or a segment thereof that retains the toxin activity of the polypeptide defined by SEQ ID NO:7.

2. The protein according to claim 1 wherein said protein comprises an amino acid sequence that has at least 90% identity with SEQ ID NO:9 and retains the toxin activity of the polypeptide defined by SEQ ID NO:9.

3. The protein according to claim 1 wherein said protein comprises an amino acid sequence that has at least 95% identity with SEQ ID NO:9 and retains the toxin activity of the polypeptide defined by SEQ ID NO:9.

4. The protein according to claim 1 wherein said protein comprises a segment of the polypeptide defined by SEQ ID NO:9 wherein said segment retains the toxin activity of said polypeptide.

5. The protein according to claim 1 wherein said protein comprises the amino acid sequence of SEQ ID NO:9.

6. A method of controlling a corn rootworm pest wherein said method comprises contacting said pest with a pesticidally effective amount of an isolated protein, wherein said protein comprises an amino acid sequence selected from the group consisting of SEQ ID NO:7 and SEQ ID NO:9.

* * * * *

UNITED STATES PATENT AND TRADEMARK OFFICE
CERTIFICATE OF CORRECTION

PATENT NO. : 6,605,701 B2
DATED : August 12, 2003
INVENTOR(S) : H. Ernest Schnepf et al.

It is certified that error appears in the above-identified patent and that said Letters Patent is hereby corrected as shown below:

Column 3,
Line 60, "H8fte" should read -- Höfte --.

Column 11,
Line 31, "may include Theological agents" should read -- may include rheological agents --.

Signed and Sealed this

Twenty-eighth Day of February, 2006

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 2645
<212> TYPE: DNA
<213> ORGANISM: Bacillus laterosporus

<400> SEQUENCE: 1
atgaagaaga agttagcaag tgttgtaacg tgtacgttat tagctcctat gtttttgaat      60
ggaaatgtga atgctgttta cgcagacagc aaaacaaatc aaatttctac aacacagaaa     120
aatcaacaga aagagatgga ccgaaaagga ttacttgggt attatttcaa aggaaaagat     180
tttagtaatc ttactatgtt tgcaccgaca cgtgatagta ctcttattta tgatcaacaa     240
```

-continued

```
acagcaaata aactattaga taaaaaacaa caagaatatc agtctattcg ttggattggt      300
ttgattcaga gtaaagaaac gggagatttc acatttaact tatctgagga tgaacaggca      360
attatagaaa tcaatgggaa aattatttct aataaaggga agaaaagca agttgtccat       420 ttagaaaaag gaaaattagt tccaatcaaa atagagtatc aatcagatac aaaatttaat      480
attgacagta aacatttaa agaacttaaa ttatttaaaa tagatagtca aaaccaaccc       540
cagcaagtcc agcaagatga actgagaaat cctgaattta acaagaaaga atcacaggaa      600
ttcttagcga aaccatcgaa aataaatctt ttcactcaaa aaatgaaaag ggaaattgat      660
gaagacacgg atacggatgg ggactctatt cctgaccttt gggaagaaaa tgggtatacg      720
attcaaaata gaatcgctgt aaagtgggac gattctytag caagtaaagg gtatacgaaa      780
tttgtttcaa atccgctaga aagtcacaca gttggtgatc cttatacaga ttatgaaaag      840
gcagcaagag acctagattt gtcaaatgca aaggaaacgt taacccatt ggtagctgct       900 tttccaagtg tgaatgttag tatggaaaag gtgatattat caccaaatga aaatttatcc      960
aatagtgtag agtctcattc atccacgaat tggtcttata caaatacaga aggtgcttct     1020
gttgaagcgg ggattggacc aaaaggtatt tcgttcggag ttagcgtaaa ctatcaacac     1080
tctgaaacag ttgcacaaga atggggaaca tctacaggaa atacttcgca attcaatacg     1140
gcttcagcgg gatatttaaa tgcaaatgtt cgatataaca atgtaggaac tggtgccatc     1200
tacgatgtaa aacctacaac aagttttgta ttaaataacg atactatcgc aactattacg     1260
gcgaaatcta attctacagc cttaaatata tctcctggag aaagttaccc gaaaaaagga     1320
caaaatggaa tcgcaataac atcaatggat gattttaatt cccatccgat tacattaaat     1380
aaaaaacaag tagataatct gctaaataat aaacctatga tgttggaaac aaaccaaaca     1440
gatggtgttt ataagataaa agatacacat ggaaatatag taactggcgg agaatggaat     1500
ggtgtcatac aacaaatcaa ggctaaaaca gcgtctatta ttgtggatga tggggaacgt     1560
gtagcagaaa aacgtgtagc ggcaaaagat tatgaaaatc cagaagataa aacaccgtct     1620
ttaactttaa aagatgccct gaagctttca tatccagatg aaataaaaga aatagaggga     1680
ttattatatt ataaaaacaa accgatatac gaatcgagcg ttatgactta cttagatgaa     1740
aatacagcaa agaagtgac caaacaatta atgatacca ctgggaaatt taagatgta       1800 agtcatttat atgatgtaaa actgactcca aaaatgaatg ttacaatcaa attgtctata     1860
ctttatgata atgctgagtc taatgataac tcaattggta aatggacaaa cacaaatatt     1920
gtttcaggtg gaaataacgg aaaaaaacaa tattcttcta ataatccgga tgctaatttg     1980
acattaaata cagatgctca agaaaaatta aataaaaatc gtactattat ataagtttat     2040
atatgaagtc agaaaaaaac acacaatgtg agattactat agatggggag atttatccga     2100
tcactacaaa aacagtgaat gtgaataaag acaattacaa aagattagat attatagctc     2160
ataatataaa aagtaatcca atttcttcaa ttcatattaa aacgaatgat gaaataactt     2220
tattttggga tgatatttct ataacagatg tagcatcaat aaaaccggaa aatttaacag     2280
attcagaaat taaacagatt tatagtaggt atggtattaa gttagaagat ggaatcctta     2340
ttgataaaaa aggtgggatt cattatgtg aatttattaa tgaagctagt tttaatattg       2400
aaccattgca aaattatgtg acaaaatata aagttactta tagtagtgag ttaggacaaa     2460
acgtgagtga cacacttgaa agtgataaaa tttacaagga tgggacaatt aaatttgatt     2520
ttacaaaata tagtraaaat gaacaaggat tattttatga cagtggatta aattgggact     2580
ttaaaattaa tgctattact tatgatggta aagagatgaa tgtttttcat agatataata     2640
```

```
aatag                                                          2645

<210> SEQ ID NO 2
<211> LENGTH: 1341
<212> TYPE: DNA
<213> ORGANISM: Bacillus laterosporus

<400> SEQUENCE: 2
atgtttatgg tttctaaaaa attacaagta gttactaaaa ctgtattgct tagtacagtt     60
ttctctatat cttttattaaa taatgaagtg ataaaagctg aacaattaaa tataaattct    120
caaagtaaat atactaactt gcaaaatcta aaatcactg acaaggtaga ggattttaaa     180
gaagataagg aaaagcgaa agaatggggg aagaaaaag aaaaagagtg gaaactaact     240
gctactgaaa aggaaaaat gaataatttt ttagataata aaaatgatat aaagacaaat     300
tataaagaaa ttacttttc tatggcaggc tcatttgaag atgaaataaa agatttaaaa     360
gaaattgata agatgtttga taaaaccaat ctatcaaatt ctattatcac ctataaaaat     420
gtggaaccga caacaattgg atttaataaa tctttaacag aagtaatac gattaattct     480 gatgcaatgg cacagtttaa agaacaattt ttagataggg atattaagtt tgatagttat     540
ctagatacgc atttaactgc tcaacaagtt tccagtaaag aaagagttat tttgaaggtt     600
acggttccga gtgggaaagg ttctactact ccaacaaaag caggtgtcat tttaaataat     660
agtgaataca aaatgctcat tgataatggg tatatggtcc atgtagataa ggtatcaaaa     720
gtggtgaaaa aaggggtgga gtgcttacaa attgaaggga ctttaaaaaa gagtcttgac     780
tttaaaaatg atataaatgc tgaagcgcat agctggggta tgaagaatta tgaagagtgg     840
gctaaagatt taaccgattc gcaaagggaa gctttagatg ggtatgctag caagattat     900 aaagaaatca ataattattt aagaaatcaa ggcggaagtg gaaatgaaaa actagatgct     960
caaataaaaa atatttctga tgctttaggg aagaaaccaa taccggaaaa tattactgtg    1020
tatagatggt gtggcatgcc ggaatttggt tatcaaatta gtgatccgtt accttctta   1080 aaagattttg aagaacaatt tttaaataca atcaaagaag acaaaggata tatgagtaca    1140
agcttatcga gtgaacgtct tgcagctttt ggatctagaa aaattatatt acgattacaa    1200
gttccgaaag gaagtacggg tgcgtattta agtgccattg gtggatttgc aagtgaaaaa    1260
gagatcctac ttgataaaga tagtaaatat catattgata aagtaacaga ggtaattatt    1320
aaggtgttaa gcgatatgta g                                             1341

<210> SEQ ID NO 3
<211> LENGTH: 20
<212> TYPE: DNA
<213> ORGANISM: Bacillus laterosporus

<400> SEQUENCE: 3
ggrttamttg grtaytattt                                                20

<210> SEQ ID NO 4
<211> LENGTH: 20
<212> TYPE: DNA
<213> ORGANISM: Bacillus laterosporus

<400> SEQUENCE: 4
atatckwaya ttkgcattta                                                20

<210> SEQ ID NO 5
```

-continued

<211> LENGTH: 1062
<212> TYPE: DNA
<213> ORGANISM: Bacillus laterosporus
<220> FEATURE:
<221> NAME/KEY: misc_feature
<222> LOCATION: (483)
<223> OTHER INFORMATION: Undetermined
<221> NAME/KEY: misc_feature
<222> LOCATION: (488)
<223> OTHER INFORMATION: Undetermined
<221> NAME/KEY: misc_feature
<222> LOCATION: (525)
<223> OTHER INFORMATION: Undetermined
<221> NAME/KEY: misc_feature
<222> LOCATION: (532)
<223> OTHER INFORMATION: Undetermined

<400> SEQUENCE: 5

```
taattggata ttattttaaa ggaaaagagt ttaatcatgt tactttgttc gcaccaacac     60
gtgataatac ccttatttat gatcaacaaa cagtagattc cttattggat aaaaaacaac    120
aagaatatca atctattcga tggattggtt tgattcaaag taaagaaacg ggtgatttca    180
catttaactt atcagatgat aaaaatgcaa ttatggaaat agatacaaaa accatttcgc    240
ataaaggaca gaacaaacaa gttgttcact tagaaaaagg aaagttagtc ccgataaaaa    300
ttgagtatca accaagacca aatagtaaat agggatagta aaatctttaa agagtttaaa    360
ttattcaaag tagatagtaa gcaacaatct ccaccaagtt caactagatg aattaagaaa    420
ccccggagtt taataaaaaa gaaacacaac attccttaga aaaagscwcc aaaaacaaat    480
ccnttttnac mcmcvrgaac cattgaaaaa gagatgaggg atgcntamcg gnatacagat    540
kggagatyyt atcycctgga cctttgggga agaaaatggg tataccaatc caaaataaag    600
ttagctggtc aaagttggra kgattccatt ccccsccgyt aaaagggtwt accaaaattt    660
ggttycyyaa yccattttga tagtcataca gttggagatc cctatactga ttatgaaaaa    720
gcagcaagag atttagactt ggcccaatgc aaaagaaaca tttaacccat tagtagctgc    780
ttttccaagt gtgaatgtga atttggaaaa agtaatatta tccccaaatg aggatttatc    840
taacagtgta gaatctcatt cgtctacaaa ttggtcttat accaatacag aaggagtttc    900
tatcgaagct gggagtggtc cattgggtat ttcttatgga gtgagtgcta attatcaaca    960
ctctgaaaca gttgcaaaag aatggggaac atctacagga aatacttcgc aatttaatac   1020
agcttcagca gggtatctaa atgccaatat tcgatataag cc                      1062
```

<210> SEQ ID NO 6
<211> LENGTH: 2355
<212> TYPE: DNA
<213> ORGANISM: Bacillus laterosporus

<400> SEQUENCE: 6

```
atgacataca tgaaaaaaaa gttagttagt gttgtaacct gtacgttatt agccccaatg     60
tttttgaatg gaaatgtaaa tcctgtttat gcagacaatc aaacaaatca gctttctaca    120
gcgcaggaaa accaagaaaa agaggtagat cgaaaaggat tactcggcta ttattttaaa    180
ggaaaagagt ttaatcatct tactttgttc gcaccaacac gtgataatac ccttatttat    240
gatcaacaaa cagtagattc cttattggat aaaaaacaac aagaatatca atctattcga    300
tggattggtt tgattcaaag taaagaaacg ggtgatttca catttaactt atcagatgat    360
aaaaatgcaa ttatggaaat agatacaaaa accatttcgc ataaaggaca gaacaaacaa    420
gttgttcact tagaaaaagg aaagttagtc ccgataaaaa ttgagtatca accagatcaa    480
```

-continued

| | |
|---|---|
| atagtaaata gggatagtaa aatctttaaa gagtttaaat tattcaaagt agatagtaag | 540 |
| caacaatctc accaagttca actagatgaa ttaagaaacc ctgagtttaa taaaaagaa | 600 |
| acacaacaat tcttagaaaa agcatcaaaa acaaatcttt ttacacagaa catgaaaaga | 660 |
| gatgaggatg ctacggatac agatggagat tctattcctg acctttggga agaaaatggg | 720 |
| tataccatcc aaaataaagt agctgtcaag tgggatgatt cattcgccgc taagggtat | 780 |
| acaaatttg tttctaatcc atttgatagt catacagttg gagatcccta tactgattat | 840 |
| gaaaagcag caagagattt agacttggcc aatgcaaaag aaacatttaa cccattagta | 900 |
| gctgcttttc caagtgtgaa tgtgaatttg gaaaagtaa tattatcccc aaatgaggat | 960 |
| ttatctaaca gtgtagaatc tcattcgtct acaaattggt cttataccaa tacagaagga | 1020 |
| gtttctatcg aagctgggag tggtccattg ggtatttctt atggagtgag tgctaattat | 1080 |
| caacactctg aaacagttgc aaaagaatgg ggaacatcta caggaaatac ttcgcaattt | 1140 |
| aatacagctt cagcagggta tctcaatgcc aatgttcgat acaataatgt gggaacaggt | 1200 |
| gcgattatg aggtgaaacc tacaacaggt tttgtgttag ataacgatac tgtagcaaca | 1260 |
| attaccgcaa aatcgaattc gacagcttta agtatatctc caggagaaag ttatccgaaa | 1320 |
| aaaggacaaa atgggattgc aattaataca atggatgatt ttaattccca tccgattaca | 1380 |
| ttaaataaac aacaattaga tcaaatattt aataataaac ctcttatgtt agaaacaaat | 1440 |
| caggcagatg gtgtttataa aataaaagat acaagcggta atattgtgac tggtggagaa | 1500 |
| tggaacggtg ttatccaaca aattcaagca aaaacagcct ctattatcgt tgatacggga | 1560 |
| gaaggtgttt cagaaaagcg tgtcgcagca aaagattatg ataatcctga ggataaaaca | 1620 |
| ccttctttgt cttaaaaga ggcacttaaa cttggatatc cagaagaaat taagaaaaa | 1680 |
| gatggattgt tgtactataa tgacaaacca atttacgaat ctagtgttat gacttatcta | 1740 |
| gatgagaata cagcaaaaga agtaaaagaa caattaaatg atatcactgg aaaatttaaa | 1800 |
| gatgtgaagc agttatttga tgtgaaactt cacctaaaa tgaattttac tatcaagtta | 1860 |
| gctacgctat atgatggagc tgaagatggg tcatctccta ctgatgtagg tatcagtagt | 1920 |
| cctttagggg aatgggcatt taaccagat ataaataatg ttgaagggg gaatactgga | 1980 |
| aaaagacaat accaattaag taaaataaa gatggttatt actatggtat gttagctcta | 2040 |
| tcaccagagg tatcaaacaa gttgaaaaaa aattatcaat actatatcag tatgtctata | 2100 |
| aaagcagatg ctggtgtgga acctacagta acagttatgg ataatttaaa ttgtatagta | 2160 |
| gataaaaaat taaaattaag tagtaacggt tatcaaagat ttgatatttt agtagataat | 2220 |
| tctgaatccc atccaataaa tgtgatggta atcgatttag gtgtaagcag ccaagattat | 2280 |
| aacaattata gtaagaatat atacattgat gatataacaa ttacagaggt ttcagctatg | 2340 |
| aaagtgaaaa attag | 2355 |

<210> SEQ ID NO 7
<211> LENGTH: 784
<212> TYPE: PRT
<213> ORGANISM: Peptide sequence

<400> SEQUENCE: 7

Met Thr Tyr Met Lys Lys Lys Leu Val Ser Val Thr Cys Thr Leu
1               5                   10                  15

Leu Ala Pro Met Phe Leu Asn Gly Asn Val Asn Pro Val Tyr Ala Asp
                20                  25                  30

Asn Gln Thr Asn Gln Leu Ser Thr Ala Gln Glu Asn Gln Glu Lys Glu

-continued

```
                35                  40                  45
Val Asp Arg Lys Gly Leu Leu Gly Tyr Tyr Phe Lys Gly Lys Glu Phe
     50                  55                  60

Asn His Leu Thr Leu Phe Ala Pro Thr Arg Asp Asn Thr Leu Ile Tyr
 65                  70                  75                  80

Asp Gln Gln Thr Val Asp Ser Leu Leu Asp Lys Lys Gln Gln Glu Tyr
                 85                  90                  95

Gln Ser Ile Arg Trp Ile Gly Leu Ile Gln Ser Lys Glu Thr Gly Asp
             100                 105                 110

Phe Thr Phe Asn Leu Ser Asp Asp Lys Asn Ala Ile Met Glu Ile Asp
         115                 120                 125

Thr Lys Thr Ile Ser His Lys Gly Gln Asn Lys Gln Val Val His Leu
     130                 135                 140

Glu Lys Gly Lys Leu Val Pro Ile Lys Ile Glu Tyr Gln Pro Asp Gln
145                 150                 155                 160

Ile Val Asn Arg Asp Ser Lys Ile Phe Lys Glu Phe Lys Leu Phe Lys
                 165                 170                 175

Val Asp Ser Lys Gln Gln Ser His Gln Val Gln Leu Asp Glu Leu Arg
             180                 185                 190

Asn Pro Glu Phe Asn Lys Lys Glu Thr Gln Gln Phe Leu Glu Lys Ala
         195                 200                 205

Ser Lys Thr Asn Leu Phe Thr Gln Asn Met Lys Arg Asp Glu Asp Ala
     210                 215                 220

Thr Asp Thr Asp Gly Asp Ser Ile Pro Asp Leu Trp Glu Glu Asn Gly
225                 230                 235                 240

Tyr Thr Ile Gln Asn Lys Val Ala Val Lys Trp Asp Asp Ser Phe Ala
                 245                 250                 255

Ala Lys Gly Tyr Thr Lys Phe Val Ser Asn Pro Phe Asp Ser His Thr
             260                 265                 270

Val Gly Asp Pro Tyr Thr Asp Tyr Glu Lys Ala Ala Arg Asp Leu Asp
         275                 280                 285

Leu Ala Asn Ala Lys Glu Thr Phe Asn Pro Leu Val Ala Ala Phe Pro
     290                 295                 300

Ser Val Asn Val Asn Leu Glu Lys Val Ile Leu Ser Pro Asn Glu Asp
305                 310                 315                 320

Leu Ser Asn Ser Val Glu Ser His Ser Ser Thr Asn Trp Ser Tyr Thr
                 325                 330                 335

Asn Thr Glu Gly Val Ser Ile Glu Ala Gly Ser Gly Pro Leu Gly Ile
             340                 345                 350

Ser Tyr Gly Val Ser Ala Asn Tyr Gln His Ser Glu Thr Val Ala Lys
         355                 360                 365

Glu Trp Gly Thr Ser Thr Gly Asn Thr Ser Gln Phe Asn Thr Ala Ser
     370                 375                 380

Ala Gly Tyr Leu Asn Ala Asn Val Arg Tyr Asn Asn Val Gly Thr Gly
385                 390                 395                 400

Ala Ile Tyr Glu Val Lys Pro Thr Thr Gly Phe Val Leu Asp Asn Asp
                 405                 410                 415

Thr Val Ala Thr Ile Thr Ala Lys Ser Asn Ser Thr Ala Leu Ser Ile
             420                 425                 430

Ser Pro Gly Glu Ser Tyr Pro Lys Lys Gly Gln Asn Gly Ile Ala Ile
         435                 440                 445

Asn Thr Met Asp Asp Phe Asn Ser His Pro Ile Thr Leu Asn Lys Gln
     450                 455                 460
```

Gln Leu Asp Gln Ile Phe Asn Asn Lys Pro Leu Met Leu Glu Thr Asn
465                 470                 475                 480

Gln Ala Asp Gly Val Tyr Lys Ile Lys Asp Thr Ser Gly Asn Ile Val
            485                 490                 495

Thr Gly Gly Glu Trp Asn Gly Val Ile Gln Gln Ile Gln Ala Lys Thr
        500                 505                 510

Ala Ser Ile Ile Val Asp Thr Gly Glu Gly Val Ser Glu Lys Arg Val
        515                 520                 525

Ala Ala Lys Asp Tyr Asp Asn Pro Glu Asp Lys Thr Pro Ser Leu Ser
530                 535                 540

Leu Lys Glu Ala Leu Lys Leu Gly Tyr Pro Glu Glu Ile Lys Glu Lys
545                 550                 555                 560

Asp Gly Leu Leu Tyr Tyr Asn Asp Lys Pro Ile Tyr Glu Ser Ser Val
            565                 570                 575

Met Thr Tyr Leu Asp Glu Asn Thr Ala Lys Glu Val Lys Glu Gln Leu
            580                 585                 590

Asn Asp Ile Thr Gly Lys Phe Lys Asp Val Lys Gln Leu Phe Asp Val
            595                 600                 605

Lys Leu Thr Pro Lys Met Asn Phe Thr Ile Lys Leu Ala Thr Leu Tyr
610                 615                 620

Asp Gly Ala Glu Asp Gly Ser Ser Pro Thr Asp Val Gly Ile Ser Ser
625                 630                 635                 640

Pro Leu Gly Glu Trp Ala Phe Lys Pro Asp Ile Asn Asn Val Glu Gly
                645                 650                 655

Gly Asn Thr Gly Lys Arg Gln Tyr Gln Leu Ser Lys Asn Lys Asp Gly
                660                 665                 670

Tyr Tyr Tyr Gly Met Leu Ala Leu Ser Pro Glu Val Ser Asn Lys Leu
            675                 680                 685

Lys Lys Asn Tyr Gln Tyr Tyr Ile Ser Met Ser Ile Lys Ala Asp Ala
            690                 695                 700

Gly Val Glu Pro Thr Val Thr Val Met Asp Asn Leu Asn Cys Ile Val
705                 710                 715                 720

Asp Lys Lys Leu Lys Leu Ser Ser Asn Gly Tyr Gln Arg Phe Asp Ile
                725                 730                 735

Leu Val Asp Asn Ser Glu Ser His Pro Ile Asn Val Met Val Ile Asp
            740                 745                 750

Leu Gly Val Ser Ser Gln Asp Tyr Asn Asn Tyr Ser Lys Asn Ile Tyr
            755                 760                 765

Ile Asp Asp Ile Thr Ile Thr Glu Val Ser Ala Met Lys Val Lys Asn
770                 775                 780

<210> SEQ ID NO 8
<211> LENGTH: 1356
<212> TYPE: DNA
<213> ORGANISM: Bacillus laterosporus

<400> SEQUENCE: 8
atggtatcta aaaagttaca attaattaca aaaactttag tgtttagtac agttttatct    60
ataccgttat tgaacaatag tgagataaaa gcggaacaat taaatatgaa ttctcaaatt   120
aaatatccta acttccaaaa tataaatatc gctgataagc cagtagattt taagaggat   180 aaagaaaaag cacgagaatg gggaaaagaa aggaaaaag agtggaaact aactgttact   240
gaaaaaggaa aataaaatga ttttttagat gataaagatg gattaaaaac aaaatataaa   300

-continued

| | |
|---|---|
| gaaattaatt tttctaagaa ctttgaatat gaaacagagt taaaagagct tgaaaaaatt | 360 |
| aataccatgc tagataaagc aaatctaaca aattcaattg tcacgtataa aaatgttgag | 420 |
| cctacaacaa taggattcaa tcaatctttg attgaaggga atcaaattaa tgccgaagct | 480 |
| caacaaaagt tcaaggaaca attttttagga caggatatta aatttgatag ttatttggat | 540 |
| atgcacttaa ctgaacaaaa tgtttccagt aaagaaaggg ttattttaaa agttacagta | 600 |
| cctagtggga aaggttctac tcccacaaaa gcaggtgttg ttttaaataa taatgaatac | 660 |
| aagatgttga ttgataatgg atatgtacta catgtagaaa acataacgaa agttgtaaaa | 720 |
| aaaggacagg aatgtttaca agttgaagga acgttaaaaa agagcttgga ctttaaaaat | 780 |
| gatagtgacg gtaagggaga ttcctgggga aagaaaaatt acaaggaatg gtctgatact | 840 |
| ttaacaactg atcaaagaaa agacttaaat gattatggtg tgcgaggtta taccgaaata | 900 |
| aataaatatt tacgtgaagg tgataccgga aatacagagt tggaggaaaa aattaaaaat | 960 |
| atttctgacg cactagaaaa gaatcctatc cctgaaaaca ttactgttta tagatattgc | 1020 |
| ggaatggcgg aatttggtta tccgattaaa cctgaggctc cttccgtaca agattttgaa | 1080 |
| gagagatttt tggatactat taaggaagaa aaaggatata tgagtacgag cttatccagt | 1140 |
| gatgcgactt cttttggtgc aagaaaaatt atattaagat tgcaagtacc aaaaggaagt | 1200 |
| tcaggagcat atgtagctgg tttagatgga tttaaacccg cagagaagga gattctcatt | 1260 |
| gataagggaa gcaagtatcg tattgataaa gtaacagaag tggttgtgaa aggtactaga | 1320 |
| aaacttgtag tcgatgctac attattaaca aaataa | 1356 |

<210> SEQ ID NO 9
<211> LENGTH: 451
<212> TYPE: PRT
<213> ORGANISM: Peptide sequence

<400> SEQUENCE: 9

```
Met Val Ser Lys Lys Leu Gln Leu Ile Thr Lys Thr Leu Val Phe Ser
 1               5                  10                  15

Thr Val Leu Ser Ile Pro Leu Leu Asn Asn Ser Glu Ile Lys Ala Glu
            20                  25                  30

Gln Leu Asn Met Asn Ser Gln Ile Lys Tyr Pro Asn Phe Gln Asn Ile
        35                  40                  45

Asn Ile Ala Asp Lys Pro Val Asp Phe Lys Glu Asp Lys Glu Lys Ala
    50                  55                  60

Arg Glu Trp Gly Lys Glu Lys Glu Trp Lys Leu Thr Val Thr
65                  70                  75                  80

Glu Lys Gly Lys Ile Asn Asp Phe Leu Asp Lys Asp Gly Leu Lys
                85                  90                  95

Thr Lys Tyr Lys Glu Ile Asn Phe Ser Lys Asn Phe Glu Tyr Glu Thr
            100                 105                 110

Glu Leu Lys Glu Leu Glu Lys Ile Asn Thr Met Leu Asp Lys Ala Asn
        115                 120                 125

Leu Thr Asn Ser Ile Val Thr Tyr Lys Asn Val Glu Pro Thr Thr Ile
    130                 135                 140

Gly Phe Asn Gln Ser Leu Ile Glu Gly Asn Gln Ile Asn Ala Glu Ala
145                 150                 155                 160

Gln Gln Lys Phe Lys Glu Gln Phe Leu Gly Gln Asp Ile Lys Phe Asp
                165                 170                 175

Ser Tyr Leu Asp Met His Leu Thr Glu Gln Asn Val Ser Ser Lys Glu
            180                 185                 190
```

-continued

```
Arg Val Ile Leu Lys Val Thr Val Pro Ser Gly Lys Gly Ser Thr Pro
        195                 200                 205
Thr Lys Ala Gly Val Val Leu Asn Asn Asn Glu Tyr Lys Met Leu Ile
    210                 215                 220

Asp Asn Gly Tyr Val Leu His Val Glu Asn Ile Thr Lys Val Val Lys
225                 230                 235                 240
Lys Gly Gln Glu Cys Leu Gln Val Glu Gly Thr Leu Lys Lys Ser Leu
                245                 250                 255
Asp Phe Lys Asn Asp Ser Asp Gly Lys Gly Asp Ser Trp Gly Lys Lys
            260                 265                 270

Asn Tyr Lys Glu Trp Ser Asp Thr Leu Thr Thr Asp Gln Arg Lys Asp
        275                 280                 285

Leu Asn Asp Tyr Gly Val Arg Gly Tyr Thr Glu Ile Asn Lys Tyr Leu
    290                 295                 300

Arg Glu Gly Asp Thr Gly Asn Thr Glu Leu Glu Glu Lys Ile Lys Asn
305                 310                 315                 320
Ile Ser Asp Ala Leu Glu Lys Asn Pro Ile Pro Glu Asn Ile Thr Val
                325                 330                 335
Tyr Arg Tyr Cys Gly Met Ala Glu Phe Gly Tyr Pro Ile Lys Pro Glu
            340                 345                 350

Ala Pro Ser Val Gln Asp Phe Glu Glu Arg Phe Leu Asp Thr Ile Lys
        355                 360                 365

Glu Glu Lys Gly Tyr Met Ser Thr Ser Leu Ser Ser Asp Ala Thr Ser
    370                 375                 380

Phe Gly Ala Arg Lys Ile Ile Leu Arg Leu Gln Val Pro Lys Gly Ser
385                 390                 395                 400
Ser Gly Ala Tyr Val Ala Gly Leu Asp Gly Phe Lys Pro Ala Glu Lys
                405                 410                 415
Glu Ile Leu Ile Asp Lys Gly Ser Lys Tyr Arg Ile Asp Lys Val Thr
            420                 425                 430

Glu Val Val Val Lys Gly Thr Arg Lys Leu Val Val Asp Ala Thr Leu
        435                 440                 445

Leu Thr Lys
    450
```

<210> SEQ ID NO 10
<211> LENGTH: 1041
<212> TYPE: DNA
<213> ORGANISM: Bacillus laterosporus

<400> SEQUENCE: 10

```
attaattggg tattatttta aaggaaaaga ttttaatgat cttaccttgt ttgcaccgac     60
acgtgataat actcttattt atgaccaaca aacagcaaat acactagtag atcaaaagca    120
tcaagaatat cattctattc gctggattgg attgattcag agtagtgcaa caggagattt    180
cacatttaaa ttgtcagatg atgaaaatgc catcattgaa ttggatggga aagttatttc    240
tgaaaaaggt aacaataaac aaagtgttca tttagaaaaa ggacagttgg tgcaaataaa    300
aattgagtac caatcagacg atgcattaca tatagataat aaaacttta aagagcttaa    360 gttattcaag atagatagtc aaaatcactc tctacaagtt caacaagatg aactgagaaa    420
ccctgagttt aataagaaag aaacgcaaag aattcttaaa gaaagcatcg aaagcaaatc    480
tttttaccgc aaaaaaccga aaagagatat tgatgaagat acggatacag atggagattc    540
tatccctgat gcttgggaag aaaacgggta taccattcaa aacaaagtag cagtcaaatg    600
```

―continued

```
ggatgattcg ttagcaagta aagggtataa aaaatttact tctaatccac tagaagcaca        660
cacagttgga gatccctata gtgattatga aaaagctgca agagatatgc ccttatcgaa        720
tgcaaaagaa acttttaatc ctctggttgc cgcctttcca tcagtaaatg ttagtttaga        780
aaaggtgatt ttatccaaaa atgaagacct ttcccatagc gttgaaagca gtcaatctac        840
caattggtct tataccaata ctgaaggcgt taacgtcaat gctggatggt caggcttagg        900
acctagtttt ggagtttctg ttaactatca acatagtgaa actgtagcca atgaatgggg        960
ttctgcgacg aatgatggca cacatataaa tggagcggaa tctgcttatt taaatgccaa       1020
tgtacgatat aagggcgaat t                                                 1041
```